United States Patent
Saffell et al.

(10) Patent No.: US 6,623,619 B2
(45) Date of Patent: Sep. 23, 2003

(54) ELECTROCHEMICAL SENSOR FOR DETERMINING ANALYTE IN THE PRESENCE OF INTERFERENT AND METHOD OF USING THE SENSOR

(75) Inventors: John R Saffell, Hampshire (GB); Michael L Hitchman, Glasgow (GB); Darryl H Dawson, Essex (GB)

(73) Assignee: Alphasense Limited (GB)

( * ) Notice: Subject to any disclaimer, the term of this patent is extended or adjusted under 35 U.S.C. 154(b) by 0 days.

(21) Appl. No.: 09/855,190

(22) Filed: May 14, 2001

(65) Prior Publication Data

US 2002/0027086 A1 Mar. 7, 2002

(30) Foreign Application Priority Data

May 13, 2000 (GB) .............................. 0011511
May 25, 2000 (GB) .............................. 0012569

(51) Int. Cl.$^7$ ..................... G01N 27/404; G01N 27/416
(52) U.S. Cl. ..................... 205/785.5; 205/783; 205/787; 204/412; 204/415; 204/431; 204/432
(58) Field of Search .............................. 204/412, 415, 204/431, 432; 205/775, 785.5, 787, 783

(56) References Cited

U.S. PATENT DOCUMENTS 4,478,704 A   10/1984  Miyoshi et al. ............. 204/412
4,808,292 A * 2/1989  Kessler et al. ......... 204/403.07
4,985,126 A * 1/1991  Haefele et al. .............. 204/406
5,466,356 A   11/1995 Schneider et al. ........... 204/406
5,635,627 A   6/1997  Bytyn ........................ 73/31.05
5,932,079 A   8/1999  Haupt et al. ................. 204/415
6,024,853 A * 2/2000  Kiesele et al. .............. 204/402
6,176,989 B1 * 1/2001  Shi ............................. 204/412

FOREIGN PATENT DOCUMENTS

DE   40 09 746 A1   10/1991
EP   0 126 623      11/1984

OTHER PUBLICATIONS

"Toxic Gas CiTicels", pp. Tox–2–Tox–39, published prior to Jul. 30, 1999.*

* cited by examiner

Primary Examiner—Nam Nguyen
Assistant Examiner—Kaj K. Olsen
(74) Attorney, Agent, or Firm—Mayer Fortkort & Williams, PC

(57) ABSTRACT

Electrochemical sensor for determining analyte in the presence of interferent, particularly carbon monoxide in the presence of hydrogen. An electrochemical cell is designed so that current flow resulting from reference electrode potential shift caused by interferent cancels out the current flow caused by interferent at the working electrode. Another electrochemical cell corrects for interferent concentration using the potential difference between a reference electrode in contact with interferent and a referent electrode not affected by inteferent.

12 Claims, 11 Drawing Sheets

SCHEMATIC OF TYPICAL TOXIC GAS
ELECTROCHEMICAL SENSOR
WITH TWO REFERENCE ELECTRODES

CURRENT - VOLTAGE CURVE FOR
TYPICAL ELECTROCHEMICAL CELL

3 ELECTRODE TOXIC SENSOR POTENTIOSTATIC
CIRCUIT FOR USE WITH FIRST EMBODIMENT

SCHEMATIC OF TOXIC GAS ELECTROCHEMICAL SENSOR WITH REDUCED SENSITIVITY TO INTERFERENT; SPECIFICALLY, A CO SENSOR WITH REDUCED HYDROGEN RESPONSE

SCHEMATIC OF TYPICAL TOXIC GAS ELECTROCHEMICAL SENSOR WITH TWO REFERENCE ELECTRODES

4 ELECTRODE TOXIC SENSOR POTENTIOSTATIC CIRCUIT FOR USE WITH SECOND EMBODIMENT

RESPONSE OF CO SENSORS TO 10 MINUTE GASSING WITH 400 ppm CO IN 400 ppm H2 BACKGROUND

SENSITIVITY TO HYDROGEN SENSOR ACCORDING TO PATENT

ELECTROCHEMICAL SENSOR FOR DETERMINING ANALYTE IN THE PRESENCE OF INTERFERENT AND METHOD OF USING THE SENSOR

FIELD OF THE INVENTION

The present invention relates in general to the field of electrochemical sensors for detecting and quantifying an analyte in the presence of an interferent. In particular, the invention relates to electrochemical toxic gas sensors which are used in an environment where there may be an interferent gas which acts to shift the potential of the electrochemical sensor's reference electrode. A specific example would be a carbon monoxide sensor for use in environments where there may also be hydrogen present.

BACKGROUND OF THE INVENTION

Electrochemical gas sensors are well known for detecting and quantifying toxic gases such as carbon monoxide, hydrogen sulphide, nitrogen oxides, chlorine, sulphur dioxide and the like. Such sensors are electrochemical cells; more specifically, they operate in an amperometric mode providing a current output which is related to the concentration of the particular analyte gas. A known sensor is shown in schematic form in FIG. 1. The sensor shown generally as 1 comprises a working electrode 2 which is typically made by sintering at an elevated temperature a mixture of catalyst (e.g. Platinum Black) and a suspension of PTFE, then pressing the sintered mixture onto a microporous PTFE membrane 3.

A disc shaped reference electrode 4 is most usually constructed similarly, again being typically a Platinum Black electrode on a microporous PTFE membrane. The counter electrode 5 is again a Platinum Black electrode in contact with an electrolyte reservoir 6, typically sulphuric acid with a concentration in the range of three to seven Molar. The electrodes are connected with electronic circuitry outside the sensor by suitable electrical contacts. A potentiostatic circuit 7 is provided which can maintain the potential of the working electrode at a constant value with respect to the reference electrode. Cell electrolyte provides ionic contact between the electrodes. A diffusion barrier 8 controls entry of gas into the sensor through a hole 9 into gas space 10.

It is known that the variation of the working electrode current (I) with applied potential (E) is broadly as shown schematically in FIG. 2. FIG. 2 illustrates that there is a plateau region of several hundred millivolts where there is very little dependence of I on E. This region of the current voltage curve is known as the diffusion, or transport limited, current plateau and occurs because the current is controlled by the diffusional flux or mass transport of the electro-active species. In this case, the toxic gas diffuses to the working electrode and this flux is independent of the potential applied to the electrode. Before and after the plateau region the current is controlled by the electrochemical kinetics of the electrode/electrolyte interface and in these regions the current is dependent on electrode potential. Therefore, toxic gas sensors are operated in the diffusion limited plateau region. For many toxic gas sensors it is found that a zero voltage applied to the working electrode with respect to the reference electrode conveniently corresponds to part of the plateau region. The transport limited current has been shown theoretically to be linearly dependent on the concentration of the toxic gas in the external environment and so an electrochemical cell operating in this mode can be effectively used for monitoring toxic gas levels.

The electrochemical reactions occurring in the cell can be illustrated by referring to what happens in a carbon monoxide sensor. At the working electrode the CO is oxidised:

$$CO+H_2O \rightarrow CO_2+2H^++2e^- \quad (R1)$$

At the counter electrode there is a counterbalancing reduction which can be represented as the reduction of hydrogen:

$$2H^++2e^- \rightarrow H_2 \quad (R2)$$

Thus the overall cell reaction is the sum of (R1) and (R2):

$$CO+H_2O \rightarrow CO_2+H_2 \quad (R3)$$

However, it is well known that in this class of carbon monoxide sensors, the predominating counter electrode reaction in air is the reduction of oxygen.

Although these sensors operate well over a large temperature range, there is a serious drawback to this type and geometry of sensor. Hydrogen gas cohabits frequently where carbon monoxide is measured and the type of carbon monoxide gas sensor illustrated in FIG. 1 will show a hydrogen cross-sensitivity of 30–60% (ie 100 ppm of hydrogen will create a current equivalent to 30–60 ppm of CO). Here, hydrogen acts as an interferent.

A strategy used for dealing with chemical interferents in other classes of chemical sensor is scrubbing the interferent with a chemical filter. However, this cannot be readily achieved for hydrogen and so the prior art has proposed several alternative ways of alleviating this source of error.

Firstly, it is known to provide a second working electrode which responds only to hydrogen. The first working electrode is sensitive to both hydrogen and carbon monoxide and the difference between the two currents, properly scaled and calibrated, should be the corrected carbon monoxide concentration. However, calibration is difficult and the sensor is prone to drift due to non-equivalent changes of catalytic activity in the two working electrodes, reducing accuracy and reliability.

Secondly, a catalyst with reduced activity appears to affect the hydrogen sensitivity more than the carbon monoxide sensitivity and so sensors with reduced catalytic activity display reduced hydrogen cross-sensitivity However, this of course reduces the signal strength and the resultant sensor shows poor performance at sub-ambient temperatures; for example a CO sensor with poor activity will show a hydrogen sensitivity of only 10%(relative to CO) but with 40% CO sensitivity at –20 C. (compared to the sensitivity at 20 C.) while a more active catalyst will show a 25 to 40% hydrogen sensitivity but with 80% CO sensitivity at –20 C. (compared to the sensitivity at 20 C.).

Thirdly, Endress and Hauser developed a low hydrogen cross sensitive carbon monoxide sensor which uses an additive in the electrolyte. However, in time the irreversibility of the reaction with the additive leads to increased cross-sensitivity reference required.

Fourthly, a bias voltage can be imposed to offset the sensor into a regime on the I-E curve where the hydrogen oxidation is less favoured than the CO oxidation, since their I-E curves will be different. However this bias voltage must be applied at all times which is a problem with portable instruments with sometimes months between use: the back-up battery for continuous biasing may be fully discharged and no longer supplying a bias voltage. This correction has been used in commercially available breath analysers for clinical CO detection.

Therefore, each of the presently available solutions results in difficult calibration, long-term drift of signal, poor temperature performance or battery problems.

SUMMARY OF THE INVENTION

The present invention aims to provide an electrochemical cell for detection of an analyte in the presence of an interferent in which the effect of the interferent is reduced or obviated. The invention aims to achieve this goal whilst providing a sensor which remains practical to calibrate, does not suffer from working electrode long-term sensitivity drift, poor temperature performance or other undesirable characteristics.

Within this specification the term "analyte" refers to a particular chemical species which is to be measured and the term "interferent" refers to a second distinct chemical species which would undergo an electrochemical reaction producing an electrical signal which leads to a signal which resembles that due to the analyte.

According to a first aspect of the present invention there is provided an electrochemical cell for sensing an analyte in the presence of an interferent, the electrochemical cell comprising a reference electrode and a working electrode connected by a potentiostatic circuit, the analyte reacting at the working electrode giving a first component of current, the interferent undergoing an electrochemical reaction giving a second component of current, the presence at the reference electrode of the interferent leading to a shift in the potential of the reference electrode, wherein the shift in the potential of the reference electrode and the action of the potentiostatic circuit leads to a third component of current, wherein properties of the electrochemical cell which affect the magnitude of the third component of current are selected so that the third component of current acts to partially, completely or over compensate for the second component of current.

Typically, the interferent might cohabit with the analyte gas or be generated by the counter electrode.

Preferably, the properties of the electrochemical cell which affect the magnitude of the third component of current are one or more of the capacitance of the working electrode, the metal on the reference electrode, the oxidation state of the metal on the reference electrode, the redox couple, capacitance or geometry of the reference electrode.

Preferably, the electrochemical cell is a gas sensor.

Preferably also, the analyte is carbon monoxide and the interferent is hydrogen.

More preferably, working electrode is a circular gas porous disk.

Preferably also, the reference electrode is an annulus, coaxial with the working electrode. More preferably, the reference electrode is at least partially exposed to the analyte gas without electrolyte between the electrode and analyte gas.

Preferably, the capacitance of the working electrode is at least 1 mF.

Typically, the electrochemical cell is used periodically. Usually this is for less than 15 minutes.

According to a second aspect of the present invention there is provided an electrochemical cell for sensing an analyte in the presence of an interferent, the electrochemical cell comprising a working electrode and a first reference electrode connected by a potentiostatic circuit, the interferent not affecting the reference electrode thus avoiding a shift in the potential of the reference electrode, the analyte reacting at the working electrode giving a first component of current, the interferent undergoing an electrochemical reaction giving a second component of current characterized in that there is further provided a second reference electrode, configured so as to be exposed to the interferent, the interferent causing a shift in the potential of the second reference electrode, the second reference electrode being connected to the first reference electrode by a potentiometric circuit for providing a measure of the potential difference between the first and second reference electrodes, said potential difference between the first and second reference electrodes being used to calculate the second component of current and thereby provide a measure of the concentration of the analyte which has reduced or no dependency on the concentration of the interferent.

Typically, the interferent cohabits with the analyte gas or is generated by the counter electrode.

Preferably, the electrochemical cell is a gas sensor.

Preferably also, the analyte is carbon monoxide and the interferent is hydrogen.

Preferably, the first reference electrode is positioned to come into contact with minimised concentrations of interferent.

Preferably, the second reference electrode is at least partially in direct contact with the analyte/interferent without electrolyte between the second reference electrode and analyte/interferent.

The provision of a measure of the concentration of the analyte which has reduced or has no dependency on the concentration of the interferent may be achieved by scaling and subtracting the inverse logarithm of the potential difference between the first and second reference electrodes from the total current measured at the working electrode.

According to a third aspect of the present invention there is provided a method for designing an electrochemical cell (1) for sensing an analyte in the presence of an interferent, the electrochemical cell comprising a reference electrode (4) and a working electrode (2) connected by a potentiostatic circuit (7), the analyte reacting at the working electrode (2) giving a first component of current, the interferent undergoing an electrochemical reaction giving a second component of current, the presence at the reference electrode (4) of the interferent leading to a shift in the potential of the reference electrode, wherein the shift in the potential of the reference electrode (4) and the action of the potentiostatic circuit (7) leads to a third component of current, the method comprising the steps of:

selecting the properties of the electrochemical cell which affect the magnitude of the third component of current so that the third component of current acts to partially, completely or over compensate for the second component of current.

According to a fourth aspect of the present invention there is provided a method for calculating the concentration of an analyte in the presence of an interferent using an electrochemical cell comprising a working electrode and a first reference electrode connected by a potentiostatic circuit and also a second reference electrode, the interferent not affecting the reference electrode thus avoiding a shift in the potential of the reference electrode, the analyte reacting at the working electrode giving a first component of current, the interferent undergoing an electrochemical reaction giving a second component of current, the second reference electrode being configured so as to be exposed to the interferent, the interferent causing a shift in the potential of the second reference electrode, the second reference electrode being connected to the first reference electrode by a potentiometric circuit for providing a measure of the potential difference between the first and second reference electrodes, the method comprising the steps of:

measuring the potential difference between the first and second reference electrodes;

thereby calculating the second component of current; and thereby providing a measure of the concentration of the analyte which has reduced or no dependency on the concentration of the interferent.

According to a fifth aspect of the present invention there is provided computer software comprising program code which, when loaded onto a computer, causes it to calculate the concentration of an analyte in the presence of an interferent by the method of the fourth aspect.

DESCRIPTION OF THE FIGURES

The present invention will now be illustrated with references to the following figures in which.

DETAILED DESCRIPTION

Figure 1:
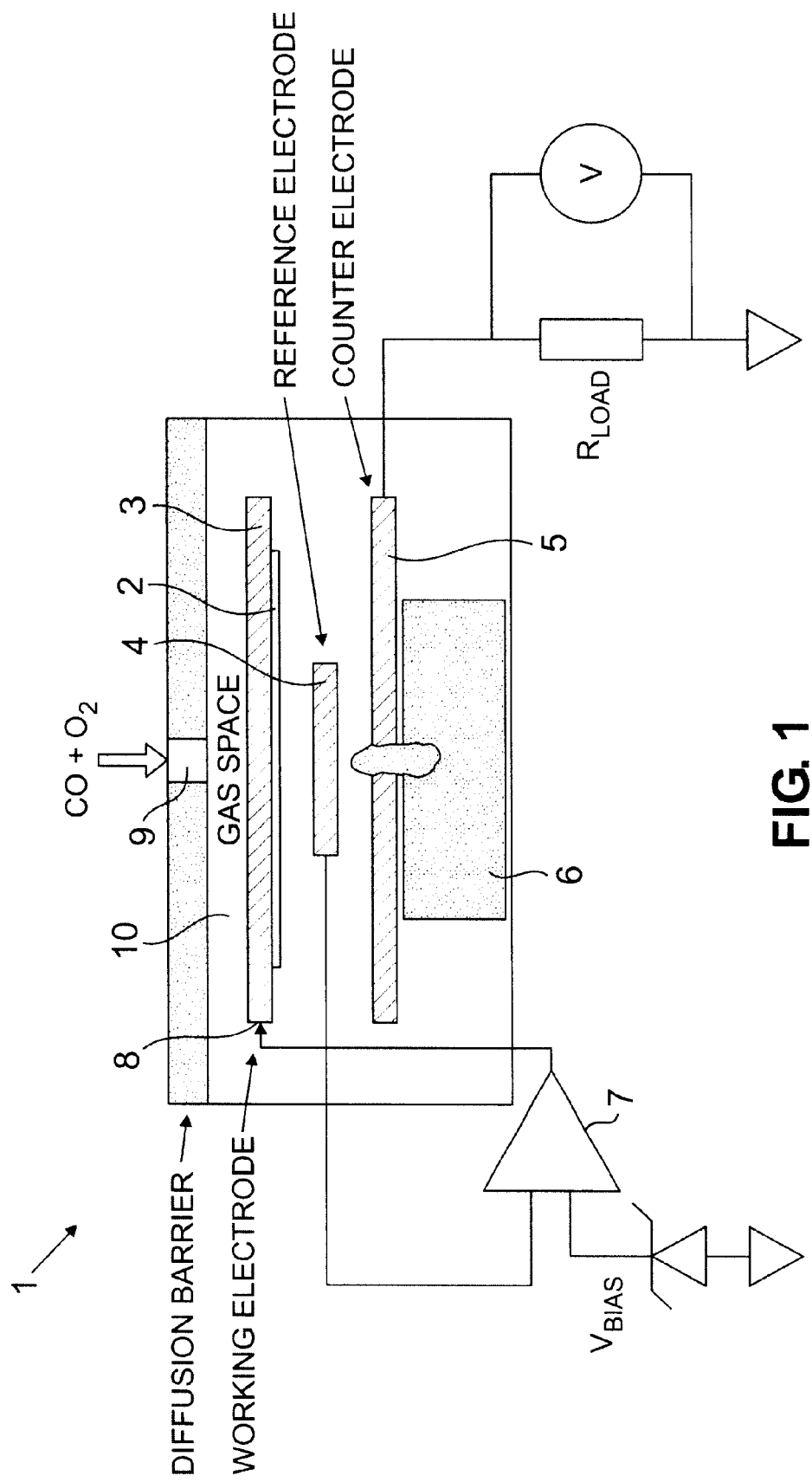
FIG. 1 shows a schematic cross-sectional view through a conventional toxic gas sensor.
Figure 2:
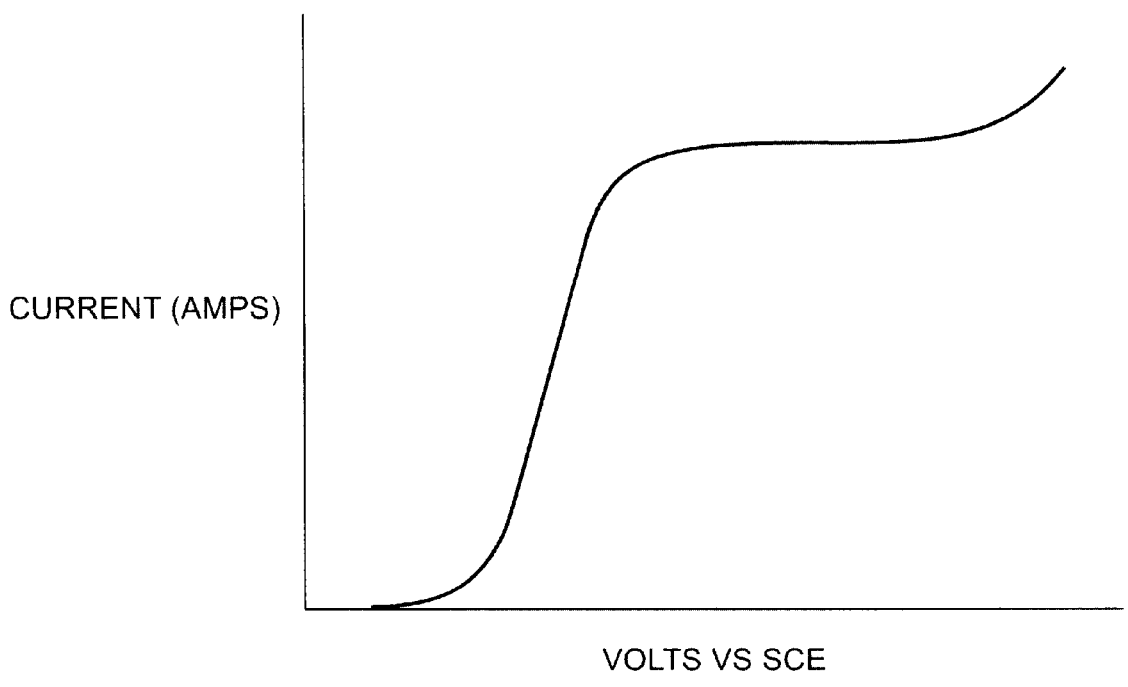
FIG. 2 is a schematic diagram of an idealised current voltage curve for a gas sensor of FIG. 1.

In a conventional carbon monoxide electrochemical sensor hydrogen acts as an interferent by diffusing through the working electrode and undergoing the following electrochemical reaction at the reference electrode:

$$2H^+ + 2e^- \leftrightarrow H_2 \tag{R2}$$

Importantly, this reference electrode reaction is taking place at the same time as the normal reference electrode reaction. The result is a mixed potential and so the presence of hydrogen shifts the potential of the reference electrode, logarithmically proportional to the hydrogen partial pressure.

As well as hydrogen in the measured gas sample, hydrogen produced by the counter electrode will also act as an interferent. This invention aims also to compensate for hydrogen produced by this mechanism. Interferent usually reacts at the working electrode but may, in some embodiments react at the counter electrode. In either case, the reaction with interferent creates a component of current measured which is not due to the analyte. The invention aims to partially, completely or overcompensate for this unwanted component of current, providing a measurement with reduced or no dependency on interferent.

The present invention is applicable to a wide range of electrochemical cells for detection of an analyte in the presence of an interferent which undergoes an electrochemical reaction at the reference electrode, the reaction having the effect of shifting the potential of the reference electrode. The phrase "in the presence of an interferent" includes both the situation where the interferent cohabits with the gas sample and when the interferent is present from any source, including being produced within the electrochemical cell (at the counter electrode in the present case).

The invention is applicable not just to the carbon monoxide gas sensor illustrated in the following example, but to other gas sensors and even fluid analyte sensors. The invention is applicable wherever an electrochemical cell having at least a working, reference and counter electrodes is used as a sensor to measure an analyte in the presence of an interferent, which either cohabits with the analyte gas or is generated by the counter electrode, which interferes by being present at the reference electrode altering the potential of that reference electrode.

We have found empirically that altering the electrode geometry affects the hydrogen cross-sensitivity of a carbon monoxide gas sensor. In particular, we have found that altering the reference electrode geometry affects the hydrogen cross-sensitivity. This would not have been predicted with present theories. The following mechanism is proposed to explain the changes in hydrogen cross-sensitivity with electrode geometry:

When hydrogen, which either cohabits with the analyte gas or is generated by the counter electrode, has direct access to the reference electrode, the reference electrode potential shifts e.g. by 15 to 30 millivolts in an example conventional carbon monoxide sensor. This small shift is not adequate to shift the sensitivity as observed on the current voltage curve and so there is only a small reduction, typically 2–3% in the carbon monoxide sensitivity, due to movement from the plateau to the kinetic region. Therefore, there is only a minimal effect on the sensitivity of the sensor.

However, the change in reference potential forces the working electrode to change its potential since the potentiometric circuit drives the working electrode to the same potential as the reference electrode (in the situation where the working electrode potential is held at zero volts relative to the reference electrode). Since the working electrode has a large capacitance, typically 20 mF, the working electrode is forced to dump charge which flows in an opposite direction to the current generated at the working electrode. This working electrode charge dumping current nullifies to some extent the hydrogen generated current with an apparent result of reduced hydrogen sensitivity.

This theory therefore predicts that hydrogen cross-sensitivity will be time dependent with the working electrode dumping charge until it is restabilised. The theory predicts that, in time, the situation will return to that where hydrogen cross-sensitivity is the same as in a standard protected reference electrode.

Changing the metal on the reference electrode and the oxidation state of the metal modifies the reference electrode rest potential and the kinetics of restabilisation of the reference electrode: both of these modify the rate of working electrode discharge and total time the working electrode discharges.

The following experimental result illustrated in FIGS. 6 to 10 demonstrates this principle.

Figure 6:
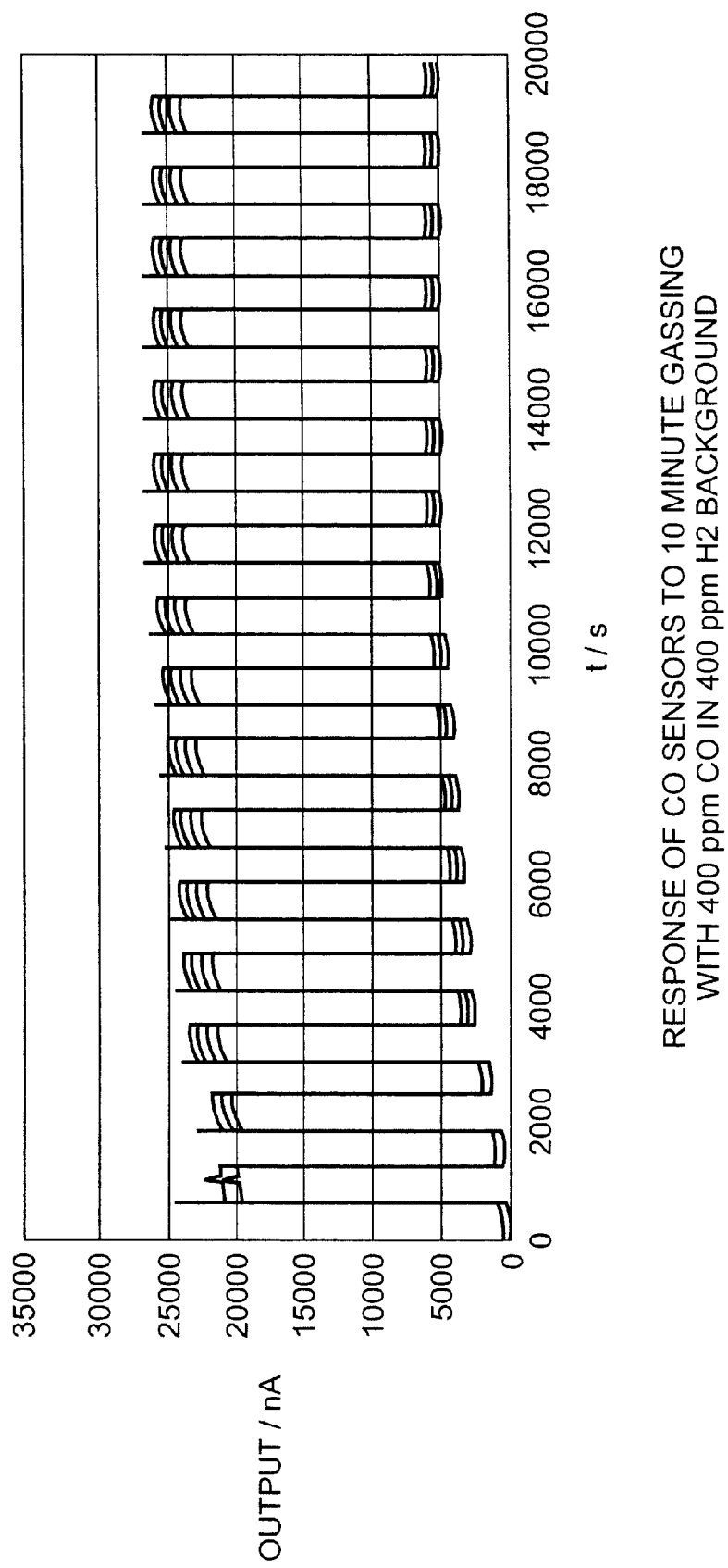
FIG. 6 shows a graph of the response with time of six sensors according to the present invention to pulses of alternately hydrogen alone and hydrogen with carbon monoxide, demonstrating increasing sensitivity to hydrogen gas with time.

In the following experiment, sensors were tested with a continuous background of 400 ppm $H_2$. Every 600 seconds, the CO would be mixed with the $H_2$ for 600 seconds. This 600 second on/off cycle was repeated 16 times. FIG. 6 shows the raw data. Each pulse increases the response to $H_2$. Around 100 minutes is required for the sensor to lose almost all of its reduced response to $H_2$.

Figure 7:
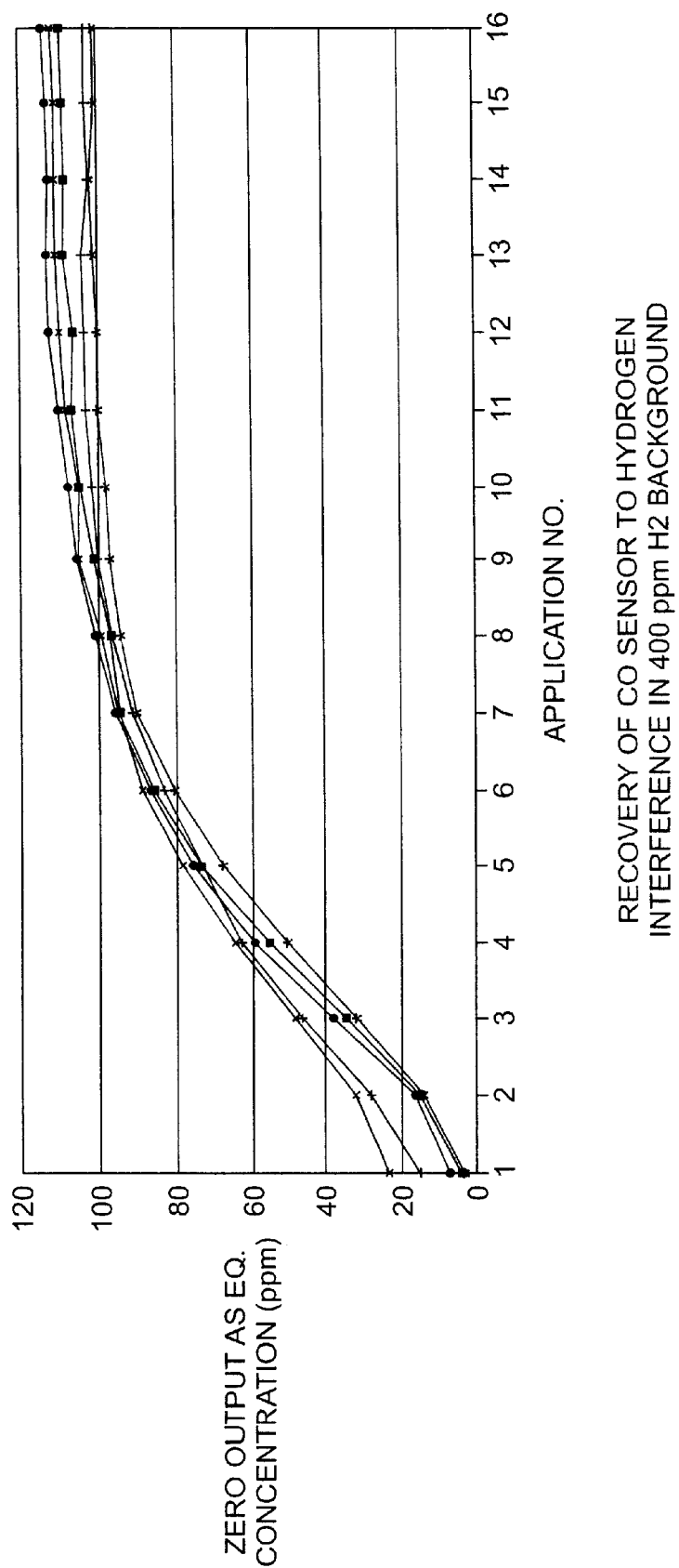
FIG. 7 illustrates how the response to a 400 ppm hydrogen background varied between consecutive cycles in the experiment of FIG. 6.

FIG. 7 shows the response to $H_2$ measured when the CO is not present. At equilibrium, the sensor responds to 400 ppm $H_2$ with a current equivalent to 100–110 ppm CO, giving a cross-interference of $$110/400=0.28.$$

Figure 8:
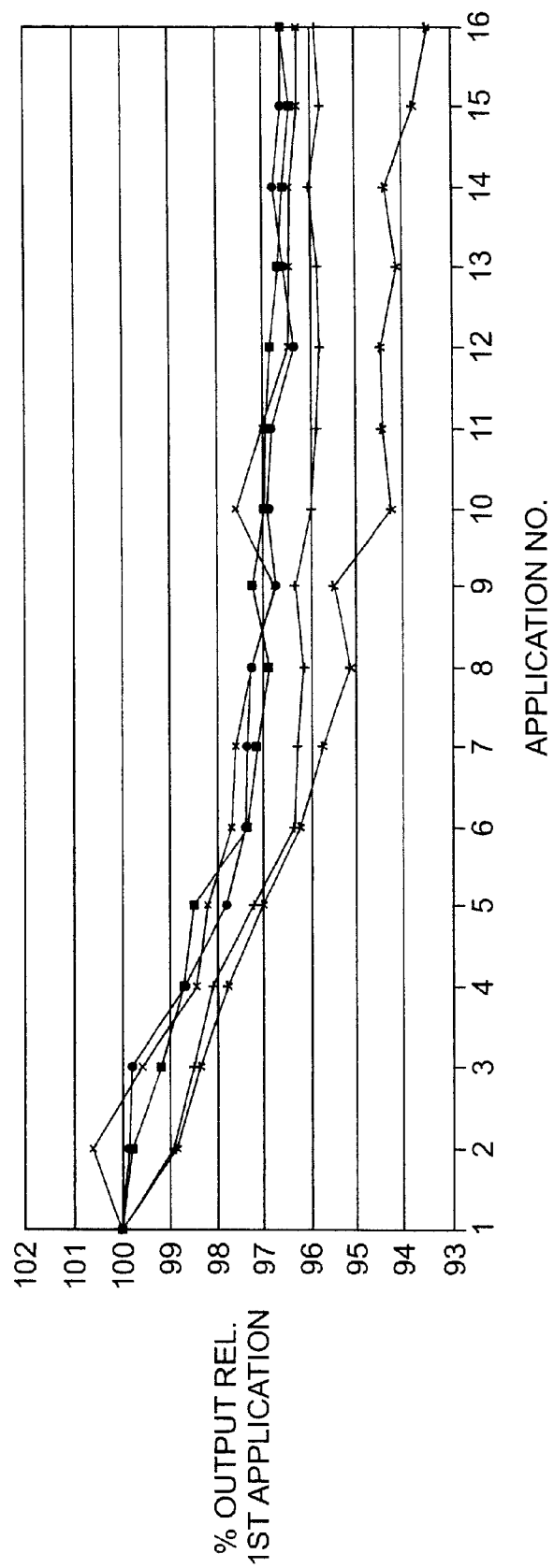
FIG. 8 shows how the signal response to carbon monoxide varied between consecutive cycles as a percentage of its initial value, in the Experiment of FIG. 6.
Figure 9:
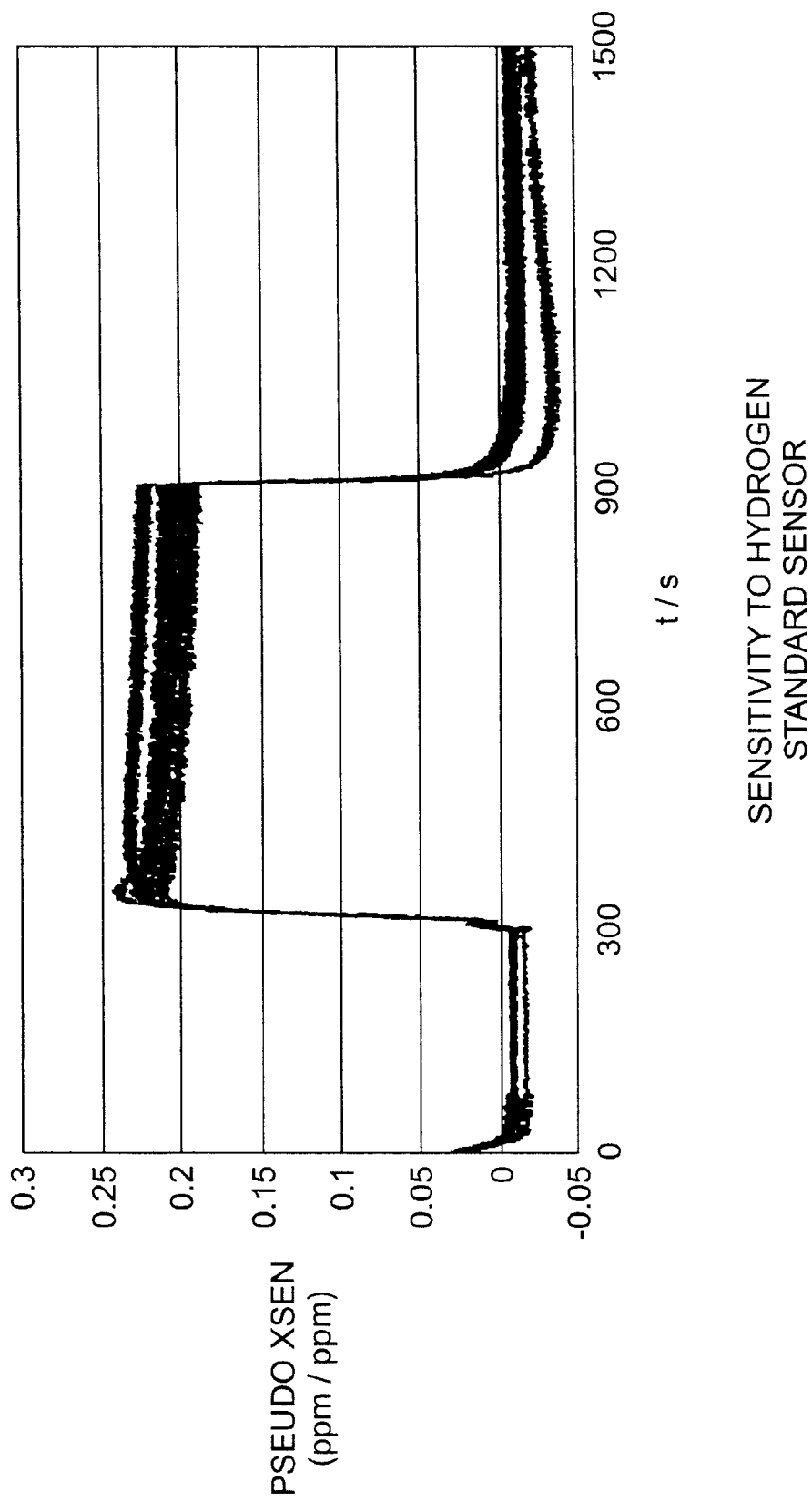
FIGS. 9 and 10 show respectively the response of a typical commercially available sensor and the sensor disclosed herein to hydrogen gas interference.
Figure 10:
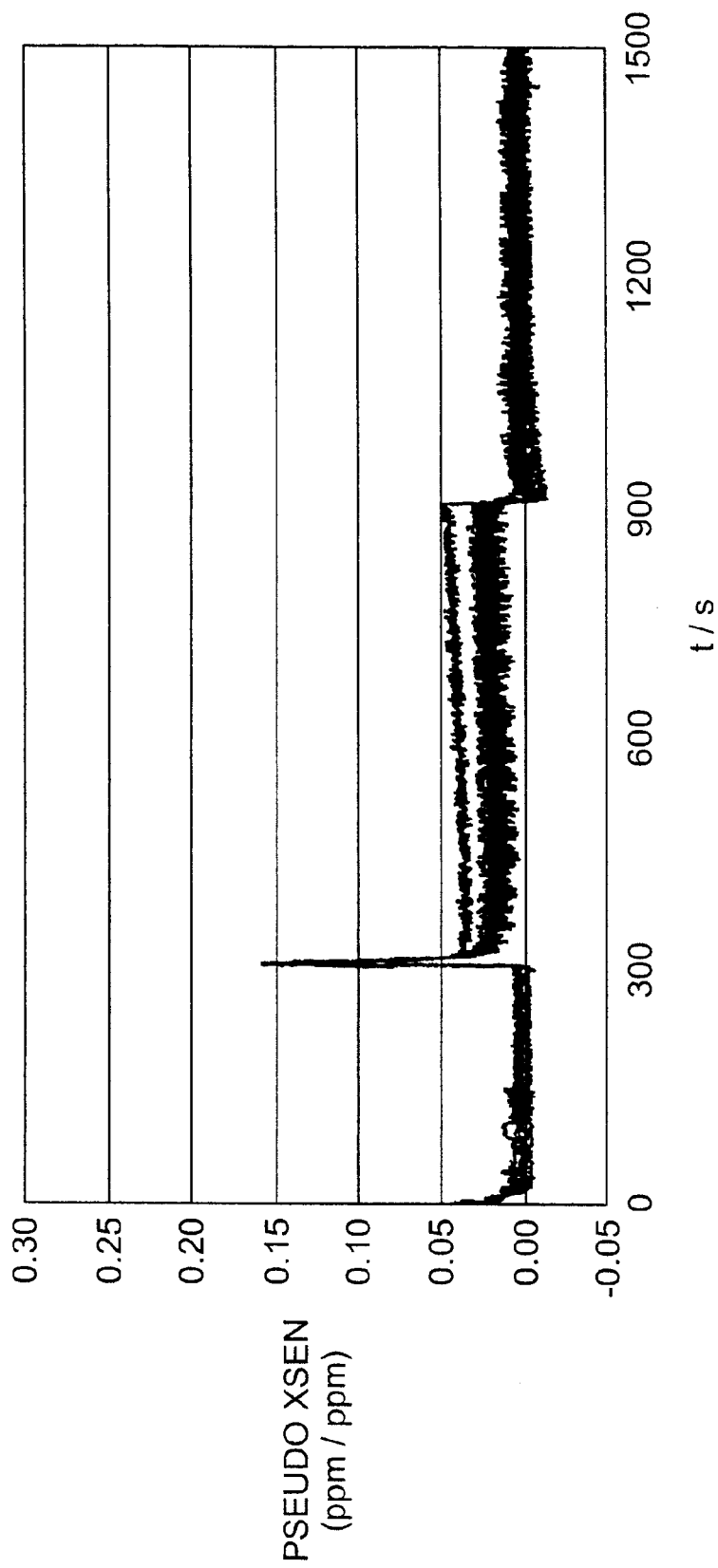

FIG. 8 shows that the working electrode loses activity after a large number of repeat measurement, perhaps due to CO poisoning the electrode or, more likely, shifting the potential by around 30 mV, moving the working electrode slightly into the kinetic region or where the current-voltage plateau is no longer flat.

In the particular examples, two hours was required for the working electrode to restabilise and return to the hydrogen cross-sensitivity typically seen with a standard reference electrode.

The theory also predicts that the cross-sensitivity would be dependent on the capacitance of the working electrode, the larger the capacitance the more current that it dumps which has the effect of countering the hydrogen generated current.

The present invention proposed involves designing the electrochemical cell by tailoring the working electrode so that its capacitance is sufficient to counter the hydrogen current. This rate of charge dumping can also be modified by changing the reference electrode redox couple or the geometry of the reference electrode. The examples below demonstrate cancellation of hydrogen current and indeed, if there is sufficient capacitance in the working electrode, negative cross-sensitivity.

Figure 3A:
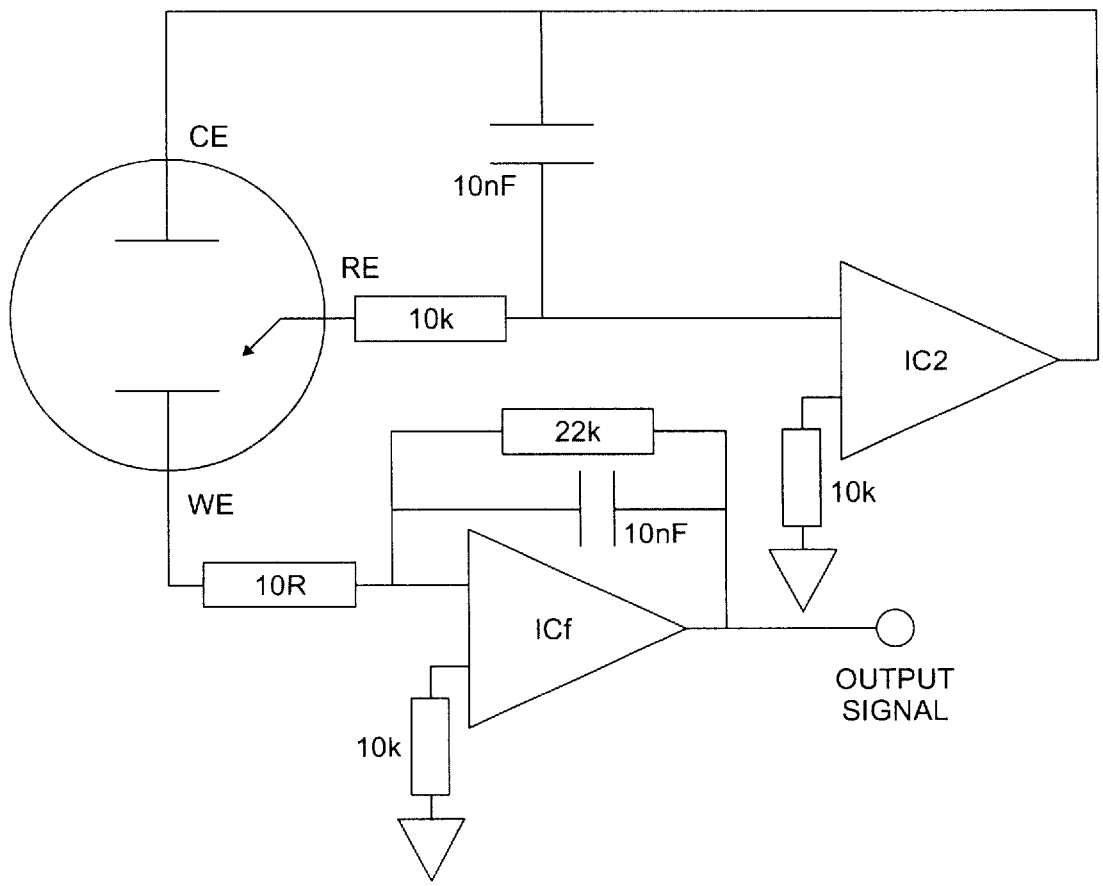
FIG. 3a is a circuit diagram of a toxic gas sensor according to the first aspect of the present invention.
Figure 3B:
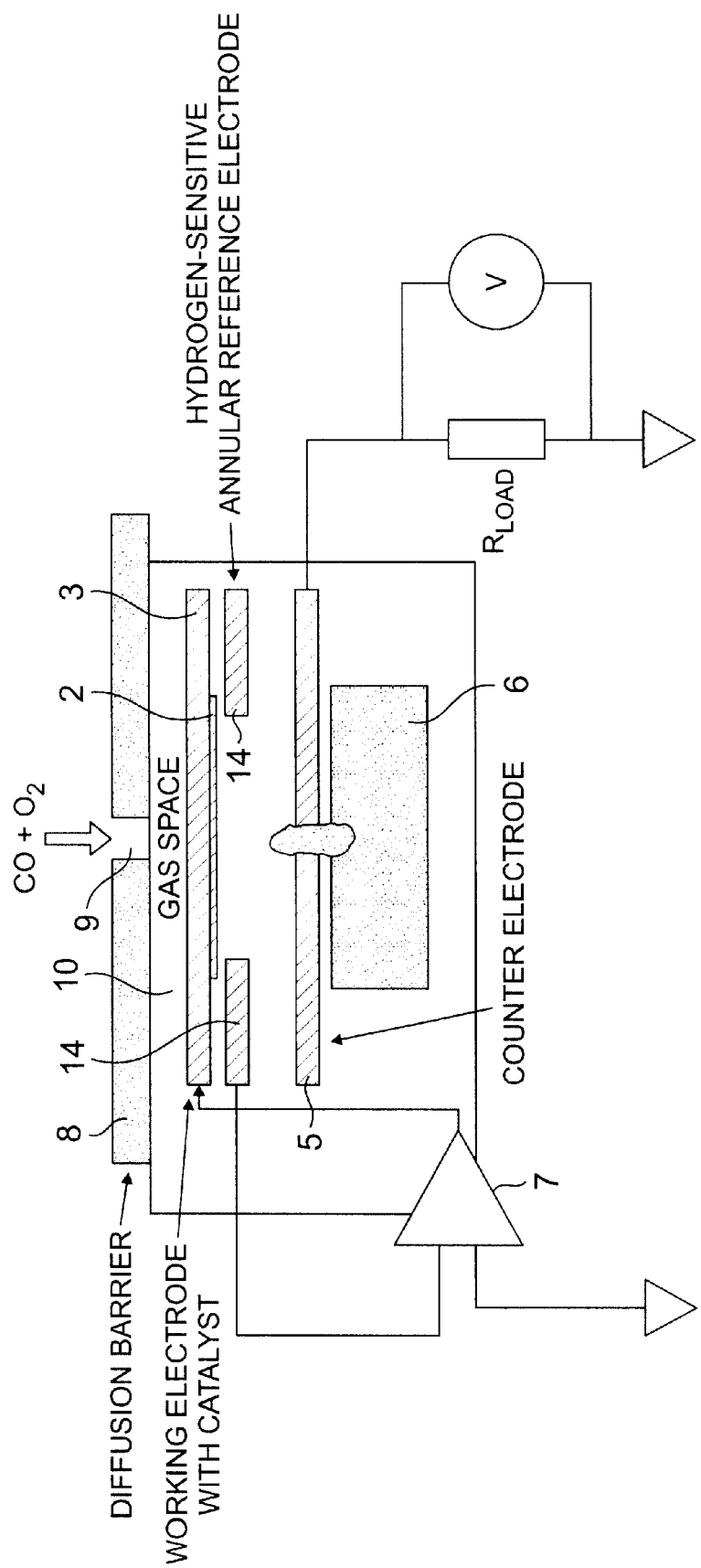
FIG. 3b is a schematic cross sectional view through a toxic gas sensor according to the first aspect of the present invention.

The preferred geometry for the reference electrode is an annulus—shown as 14 in FIG. 3b, coaxial with the working electrode and positioned to be in direct contact with hydrogen which has diffused around the edge of the working electrode 2 and porous PTFE membrane 3. However, it will be clear to one skilled in the art that alternative geometries are possible and that the key term is matching the capacitance of the working electrode to the particular geometry and chemistry of an individual sensor. In an example embodiment we have used a system where the working electrode membrane is 17.5 mm diameter with a catalyst area of 13 mm diameter. The reference electrode is also a 17.5 mm diameter membrane with an annular catalyst area with 8 mm internal diameter and 13 mm outer diameter. These dimensions were used in the examples disclosed herein, however they have not yet been fully optimised and it may be found by standard experimentation and optimisation techniques that different sizes and relative scales are better.

In a first embodiment, a three electrode system is provided which matches the working electrode capacitance to the hydrogen generated current to get a low apparent hydrogen cross-sensitivity. This is, of course, time dependent and so it will find best use in short term monitoring situations which allow time for the sensor to recover between individual readings eg it would be particularly useful for breath analysis and spot checks of CO in flue gas emissions.

Figure 4:
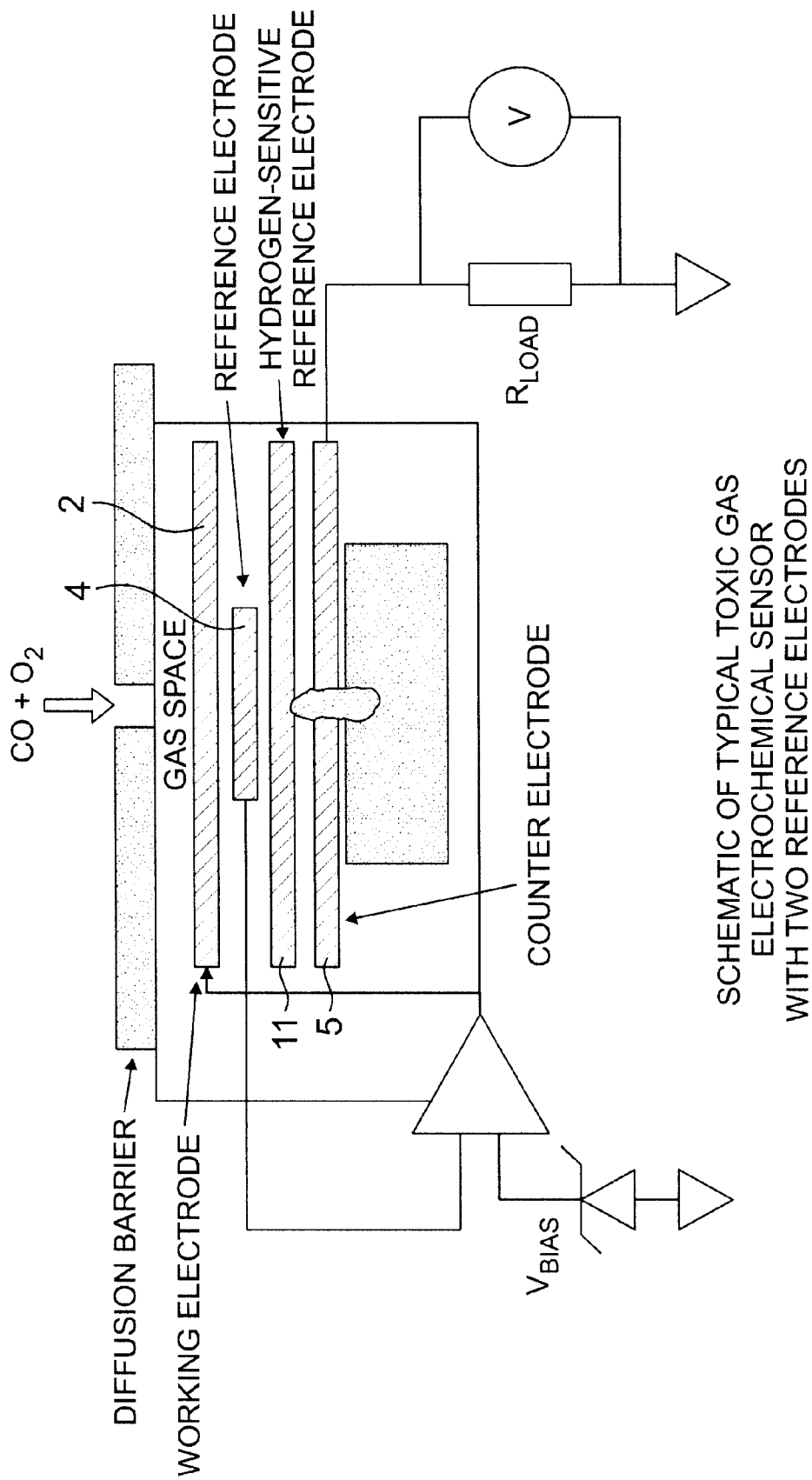
FIG. 4 is a schematic cross-section through a toxic gas sensor according to the second aspect of the present invention.

A second embodiment of the present invention provides a different, related approach to correct for hydrogen cross-sensitivity. In the second example embodiment, a second reference electrode is provided as illustrated in FIG. 4. A first reference electrode 4 is well protected underneath the working electrode 2 in exactly the same fashion as is known in the prior art. This referenced electrode functions to drive the working electrode and the working electrode potential does not change when hydrogen gas is present. The novelty lies in the second reference electrode 11 which is positioned away from the working electrode area, preferably in the form of an annulus outside the working electrode area, with direct access to the interferent, which either cohabits with the analyte gas or is generated by the counter electrode 5. The second reference electrode 11 is positioned so that its potential is changed by the presence of hydrogen gas. As with the first embodiment of this invention, it is applicable wherever there is a situation where an interferent is present at the reference electrode, shifting the potential of that reference electrode. This embodiment is stable with time, so has applications of continuous monitoring such as in coal mines and where batteries are being charged, having a continuous background of hydrogen.

Figure 5:
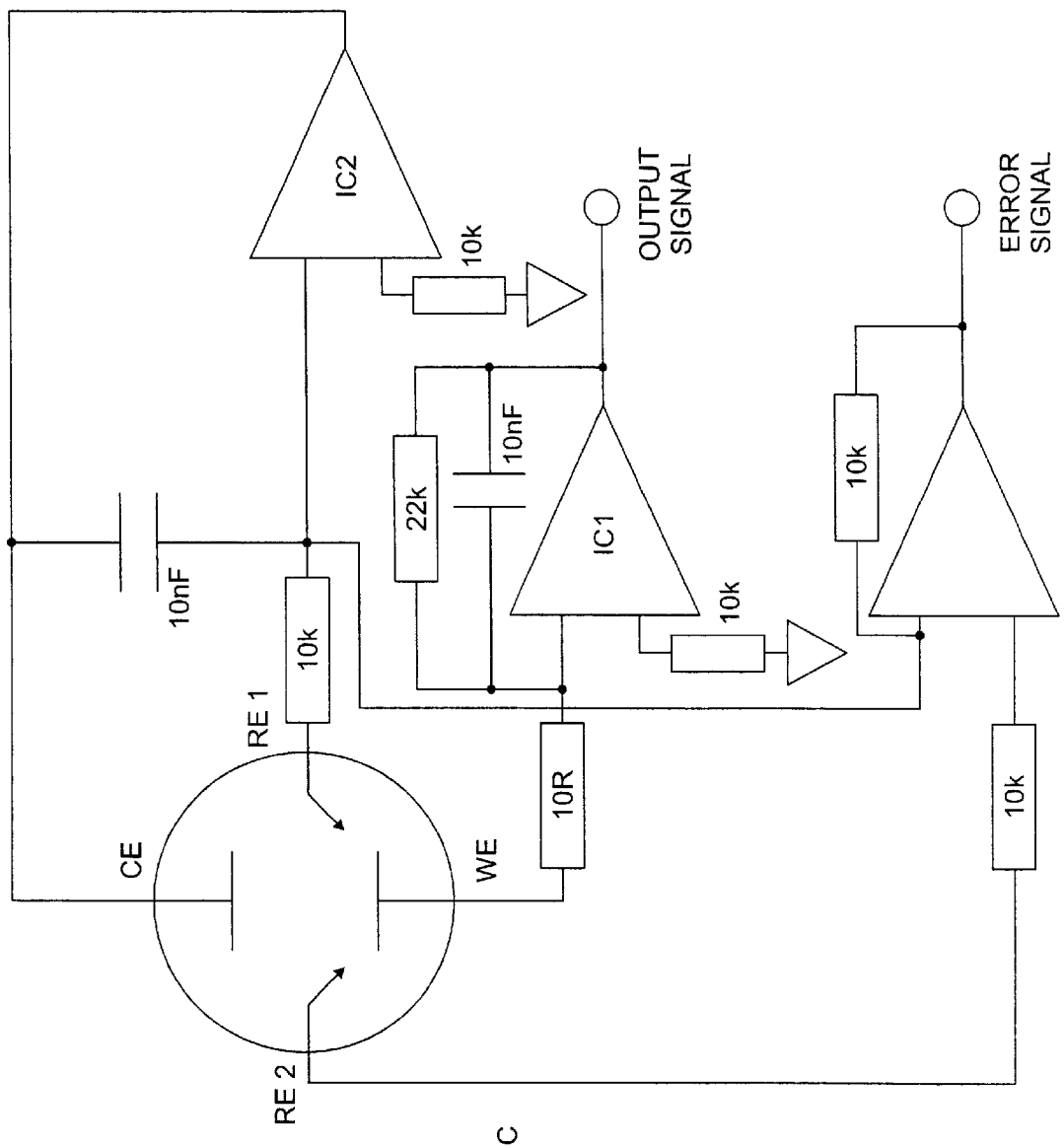
FIG. 5 shows a circuit diagram of a toxic gas sensor according to the second aspect of the present invention.

FIG. 5 shows the circuit diagram envisaged in the present embodiment. An amperometric circuit is used to measure the current into the working electrode and a potentiometric circuit is used to measure the difference between the potential of the two reference electrodes. The first conventional electrode is protected from hydrogen whereas the second is exposed. The potential difference between these reference electrodes is used as a correction signal to enable calculation of current generated by hydrogen and CO separately.

Correction may be achieved electronically or through software executed on a computer. Said software may be provided on a digital storage means such as a magnetic or optical disk or solid state storage device such as EEPROM.

We note that the potential difference between the two reference electrodes would be logarithmically dependent on the hydrogen partial pressure whilst the working electrode current would be linearly dependent on the analyte and hydrogen concentration. Software or hardware could readily be used to apply an anti-log linearisation on the hydrogen correction term. That is to say:

$$I_{corrected} = I_{measured} - k \cdot e^{(\frac{-2F}{RT})\Delta E}$$

Over a very limited hydrogen concentration range this anti-log correction may be approximated as a linear dependence.

$$I_{corrected} = I_{measured}^{-k \cdot (1-(2F/RT)\Delta E)}$$

$I_{measured}$ is the measured current, containing a component due to hydrogen, $I_{corrected}$ is the current after compensation of hydrogen, k is a constant and $\Delta E$ is the measured potential difference between the two reference electrodes.

It is known at the present time to use two working electrodes in an electrochemical cell for detection of an analyte in which the second working electrode is configured to measure the concentration of an interferent. Scaling and subtraction is then used to provide a measure of the analyte only. However, these systems require calibration with respect to both the analyte and the interferent, reducing the accuracy, precision and reproducibility of such a sensor, as well as increasing its tendency to drift.

We are not aware of a double reference electrode system being used for correction of interferents. A key advantage of the double reference electrode system proposed herein is that it requires to be calibrated only with respect to CO, improving its reliability, sensitivity and accuracy and also reducing drift. We have shown that this embodiment is repeatable between sensors.

Furthermore, the double working electrode design requires regular calibration as any change in the activity of either electrode affects the calibration. In the present invention only the reference electrode potential changes. This potential is more stable than the working electrode activity. Therefore, problems of drift will be substantially better than in the case of the double working electrode design.

It will be clear to one skilled in the art that the invention disclosed herein is applicable not just to carbon monoxide sensing in the presence of hydrogen, but to the detection of any gas in the presence of an interferent which shifts the potential of a reference electrode. Indeed, it will be clear to one skilled in the art that the invention may be readily adapted to function with solution based electrochemical cells and the detection of analytes in solution.

Further modifications and improvements may be made within the scope of the invention herein disclosed.

what is claimed is:

1. An electrochemical cell for sensing an analyte in the presence of an interferent that undergoes an electrochemical reaction to give a second component of current, the apparatus comprising:
    a working electrode adapted to react with the analyte to give a first component of current;
    a first reference electrode that does not undergo a shift in its potential upon exposure to the interferent;
    a second reference electrode adapted to undergo a shift in its potential upon exposure to the interferent;
    a potentiostatic circuit connecting the working electrode and the first reference electrode; and
    a potentiometric circuit connecting the second reference electrode and the first reference electrode, said potentiometric circuit being adapted to provide a measure of the potential difference between the first and second reference electrodes.

2. The electrochemical cell of claim 1, wherein the device is adapted to use the potential difference between the first and second reference electrodes to calculate the value of the second component of current and thereby provide a measure of the concentration of the analyte which has reduced or no dependency on the concentration of the interferent.

3. The electrochemical cell of claim 1, wherein the interferent cohabits with the analyte gas.

4. The electrochemical cell of claim 1, further comprising a counter electrode, and wherein the interferent is generated by the counter electrode.

5. The electrochemical cell of claim 1, wherein the electrochemical cell is a gas sensor.

6. The electrochemical cell of claim 5, wherein the analyte is carbon monoxide and wherein the interferent is hydrogen.

7. The electrochemical cell of claim 1, wherein the first reference electrode is positioned to come into contact with minimized concentrations of interferent.

8. The electrochemical cell of claim 1, wherein the second reference electrode is at least partially in direct contact with the analyte without electrolyte between the second reference electrode and analyte.

9. A method for determining the concentration of an analyte in the presence of an interferent with the electrochemical cell of claim 1, comprising the steps of:
    measuring the potential difference between the first and second reference electrodes, thereby determining the second component of current; and
    using the second component of current to determine the concentration of the analyte.

10. The method of claim 9, wherein the concentration of the analyte determined from the second component of current has reduced or no dependency on the concentration of the interferent.

11. The method of claim 9, wherein the concentration of the analyte is determined by measuring the total current at the working electrode, and scaling and subtracting the inverse logarithm of the potential difference between the first and second reference electrodes from the total current measured at the working electrode.

12. The method of claim 9, wherein the analyte is carbon monoxide, and wherein the interferent is hydrogen.

* * * * *